(12) United States Patent
Alqahtani et al.

(10) Patent No.: US 10,758,881 B2
(45) Date of Patent: Sep. 1, 2020

(54) METHOD FOR PROCESSING AN OLIGOMERIZATION PRODUCT STREAM

(71) Applicants: SABIC GLOBAL TECHNOLOGIES B.V., Bergen op Zoom (NL); LINDE AG, Munich (DE)

(72) Inventors: Abdullah Alqahtani, Riyadh (SA); Shahid Azam, Riyadh (SA); Anina Wöhl, Munich (DE); Wolfgang Müller, Munich (DE); Andreas Meiswinkel, Munich (DE); Heinz Bölt, Munich (DE); Ralf Noack, Munich (DE); Andreas Metzner, Munich (DE); Andre Porebski, Munich (DE); Tobias Meier, Munich (DE)

(73) Assignees: SABIC GLOBAL TECHNOLOGIES B.V., Bergen op Zoom (NL); LINDE AG, Munich (DE)

( * ) Notice: Subject to any disclaimer, the term of this patent is extended or adjusted under 35 U.S.C. 154(b) by 0 days.

(21) Appl. No.: 16/087,080

(22) PCT Filed: Mar. 17, 2017

(86) PCT No.: PCT/IB2017/051569
§ 371 (c)(1),
(2) Date: Sep. 20, 2018

(87) PCT Pub. No.: WO2017/163158
PCT Pub. Date: Sep. 28, 2017

(65) Prior Publication Data
US 2019/0105625 A1    Apr. 11, 2019

Related U.S. Application Data

(60) Provisional application No. 62/310,957, filed on Mar. 21, 2016.

(51) Int. Cl.
*B01J 4/00* (2006.01)
*B01J 19/24* (2006.01)
(Continued)

(52) U.S. Cl.
CPC .................. *B01J 4/001* (2013.01); *B01J 4/00* (2013.01); *B01J 4/008* (2013.01); *B01J 19/24* (2013.01);
(Continued)

(58) Field of Classification Search
CPC . B01J 4/001; B01J 31/34; B01J 31/143; B01J 4/008; B01J 19/24; B01J 2531/62;
(Continued)

(56) References Cited

U.S. PATENT DOCUMENTS 7,763,685 B2    7/2010    Michielin et al.
8,524,972 B1    9/2013    Weber et al.
(Continued)

FOREIGN PATENT DOCUMENTS

EP    1947075 A1    7/2008
EP    2106854 A1    10/2009
(Continued)

OTHER PUBLICATIONS

International Search Report of the International Searching Authority for International Application No. PCT/IB2017/051569; International Filing Date: Mar. 17, 2017; dated May 29, 2017; 6 pages.
(Continued)

*Primary Examiner* — Ali Z Fadhel
(74) *Attorney, Agent, or Firm* — Cantor Colburn LLP

(57) ABSTRACT

A method for processing an oligomerization product stream includes discharging the oligomerization product stream from an oligomerization reactor through a product outlet line, and heating the oligomerization product stream, heating a wall of the product outlet line, or both. The oligomeriza-
(Continued)

tion product stream includes solvent, linear alpha olefins, a polymer byproduct, or a combination of at least one of the foregoing. The heating is to a temperature that is greater than the melting temperature of the polymer byproduct present in the oligomerization product stream.

19 Claims, 1 Drawing Sheet

(51) Int. Cl.

| | | |
|---|---|---|
| C07C 7/00 | (2006.01) | |
| C10G 50/00 | (2006.01) | |
| C10G 75/00 | (2006.01) | |
| B01J 31/14 | (2006.01) | |
| B01J 31/34 | (2006.01) | |
| C07C 11/02 | (2006.01) | |
| C07C 2/32 | (2006.01) | |

(52) U.S. Cl.
CPC ............ *B01J 31/143* (2013.01); *B01J 31/34* (2013.01); *C07C 7/00* (2013.01); *C07C 11/02* (2013.01); *C10G 50/00* (2013.01); *C10G 75/00* (2013.01); B01J 2219/00054 (2013.01); B01J 2219/00092 (2013.01); B01J 2231/12 (2013.01); B01J 2531/31 (2013.01); B01J 2531/48 (2013.01); B01J 2531/62 (2013.01); *C07C 2/32* (2013.01); *C07C 2531/14* (2013.01); *C07C 2531/22* (2013.01); *C07C 2531/34* (2013.01); *C07C 2531/38* (2013.01)

(58) Field of Classification Search
CPC ................ B01J 2531/48; B01J 2531/31; B01J 2231/12; B01J 2219/00092; B01J 2219/00054; B01J 4/00; C07C 11/02; C07C 7/00; C07C 2531/38; C07C 2531/34; C07C 2531/22; C07C 2531/14; C07C 2/32; C10G 75/00; C10G 50/00
See application file for complete search history.

(56) References Cited

U.S. PATENT DOCUMENTS

| | | | |
|---|---|---|---|
| 2005/0020866 A1* | 1/2005 | Kobayashi | C07C 2/30 585/502 |
| 2009/0221769 A1 | 9/2009 | Fritz et al. | |
| 2010/0191029 A1* | 7/2010 | Fritz | C07C 2/30 585/522 |
| 2013/0144024 A1* | 6/2013 | Lattner | B01J 8/005 526/352 |
| 2014/0142360 A1* | 5/2014 | Brown | C07C 2/36 585/512 |
| 2017/0210680 A1 | 7/2017 | Azam et al. | |
| 2018/0237360 A1* | 8/2018 | Han | C07C 11/02 |

FOREIGN PATENT DOCUMENTS

| | | |
|---|---|---|
| EP | 2489431 A1 | 8/2012 |
| GB | 1564889 | 4/1980 |
| JP | 59210910 A | 11/1984 |
| WO | 2004056479 A1 | 7/2004 |

OTHER PUBLICATIONS

Written Opinion of the International Searching Authority for International Application No. PCT/IB2017/051569; International Filing Date: Mar. 1, 2017; dated May 29, 2017; 6 pages.

* cited by examiner

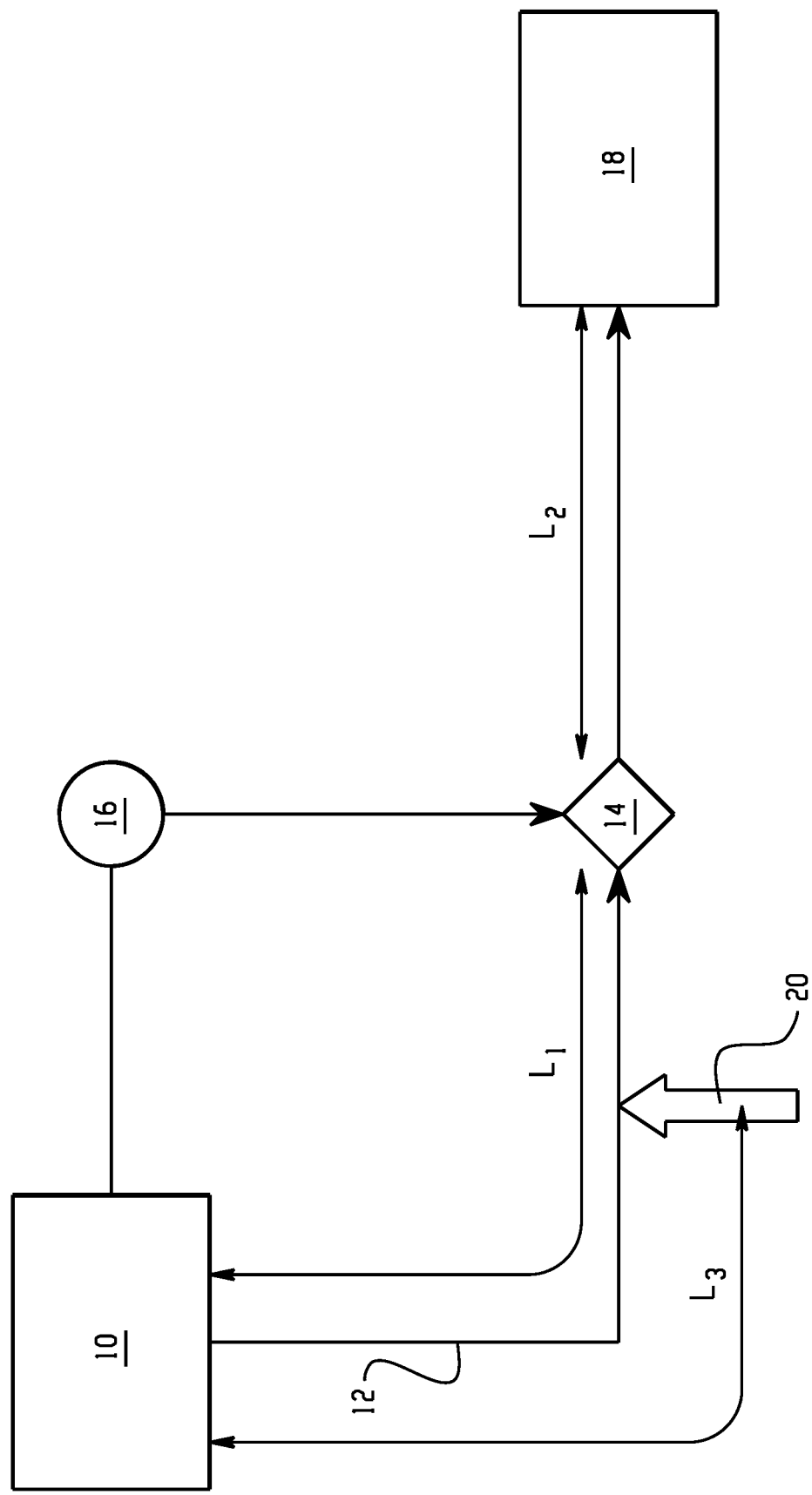

METHOD FOR PROCESSING AN OLIGOMERIZATION PRODUCT STREAM

CROSS REFERENCE TO RELATED APPLICATIONS

This application is a National Stage application of PCT/IB2017/051569, filed Mar. 17, 2017, which claims the benefit of U.S. Provisional Application No. 62/310,957, filed Mar. 21, 2016, both of which are incorporated by reference herein in their entirety.

BACKGROUND

Methods for oligomerization of ethylene and other alpha olefins are widely known. Such oligomerization methods include oligomerizing the monomer (e.g., ethylene) in a reactor in the presence of catalyst, co-catalyst and solvent. Following oligomerization in the reaction, product material comprising oligomer and/or polymer, non-reacted monomer(s), catalyst, co-catalyst and solvent can be discharged from the reactor and can be further processed. Suitable further processing can include catalyst deactivation, separation of solvent and oligomer product, and oligomer fractionation. The oligomerization methods can be operated continuously such that unreacted monomer or solvent can be recirculated in the oligomerization plant.

At times, the oligomerization reactors and other plant equipment, in particular reactor piping, require cleaning, as fouling or plugging can occur at the walls of the piping. One method to clean the reactor piping has been to flush the piping with a flushing medium, preferably at an elevated temperature. This process, however, can be undesirable because flushing the piping and reactor equipment generally produces significant quantities of contaminated flushing medium to be disposed of. Disposing of the contaminated flushing medium is often difficult and cost-intensive.

Accordingly, there is a continuing need for a process for processing an oligomerization product stream such that fouling or plugging of reactor piping is reduced or eliminated. It would be particularly advantageous to avoid the need for use of costly imported flushing medium that requires the installation of additional processing equipment and disposal through difficult and cost-intensive means.

BRIEF DESCRIPTION

Disclosed in various embodiments are methods for processing an oligomerization product stream and processes for the oligomerization of an olefin.

A method for processing an oligomerization product stream comprises discharging the oligomerization product stream from an oligomerization reactor through a product outlet line, wherein the oligomerization product stream comprises solvent, linear alpha olefins, a polymer byproduct, or a combination comprising at least one of the foregoing; and heating the oligomerization product stream, heating a wall of the product outlet line, or both, to a temperature greater than the melting temperature of the polymer byproduct.

A method for processing an oligomerization product stream comprises discharging the oligomerization product stream from an oligomerization reactor through a product outlet line having a first portion and a second portion, wherein the first and the second portions each independently have a predetermined length; wherein the first portion is configured to receive the oligomerization product stream from the oligomerization reactor; the second portion is configured to provide the oligomerization product stream to a separation system, the second portion preferably having a length of 50 to 100 meters; the first and second portions are connected by a control valve; and the oligomerization product stream comprises solvent, linear alpha olefins, residual olefin, residual catalyst, a polymer byproduct, or a combination comprising at least one of the foregoing; contacting the oligomerization product stream with a deactivation medium, wherein the contacting occurs at a minimum distance from the oligomerization reactor outlet, preferably at a distance of 0.5 to 2.0 meters downstream from the oligomerization reactor; heating the oligomerization product stream in a heat exchanger, heating a wall of the product outlet line, or both, to a temperature of 130 to 200° C., or 150 to 200° C.; and separating the linear alpha olefins from the oligomerization product stream in the separation system.

The above described and other features are exemplified by the following FIGURE and detailed description.

BRIEF DESCRIPTION OF THE DRAWINGS

The following FIGURE is an exemplary embodiment wherein the like elements are numbered alike.

FIG. 1 shows a schematic illustration of an oligomerization reactor system for employing the method for processing an oligomerization product stream.

DETAILED DESCRIPTION

Described herein is a method for processing an oligomerization product stream. It was unexpectedly discovered that fouling or plugging of the piping of an oligomerization reactor could be reduced or prevented by adjusting the temperature of the reactor product stream (e.g., by heating the oligomerization product stream itself, by heating the wall of the outlet line piping, or both), desirably to above the melting temperature of any polymer byproducts present in the product stream. Furthermore, the tube lengths of the reactor piping can be optimized (e.g., minimized) to further reduce fouling. Advantageously, using the methods described herein, the on-stream time of an oligomerization reactor can be increased, therefore minimizing production loss due to reactor downtime. Additionally, effort and cost for additional reactor cleaning are reduced due to longer operation time between reactor shutdown for cleaning.

Accordingly, one aspect of the present disclosure is a method for processing an oligomerization product stream. The method can include discharging the oligomerization product stream from an oligomerization reactor through a product outlet line, wherein the oligomerization product stream comprises solvent, linear alpha olefins, a polymer byproduct, or a combination comprising at least one of the foregoing, and heating the oligomerization product stream, heating a wall of the product outlet line, or both, to a temperature greater than the melting temperature of the polymer byproduct. For example, in some embodiments, the oligomerization product stream can be heated to a temperature of greater than 130° C., but desirably not exceeding a temperature of 200° C. For example, the oligomerization product stream can be heated to a temperature of 130 to 200° C., or 150 to 200° C.

In some embodiments, the method described herein can be as shown in FIG. 1. As shown in FIG. 1, an oligomerization product stream can be discharged from an oligomerization reactor (10) into product outlet line (12). In some embodiments, the product outlet line (12) can have a first portion ($L_1$) and a second portion ($L_2$). The first and second portions can be connected by a control valve (14). In some embodiments, the control valve can be a rotary plug valve. Levels in the oligomerization reactor can be controlled by level controller (16), which can be any suitable level controller. The level controller maintains a constant liquid level in the oligomerization reactor. A portion of the linear alpha olefin products can be withdrawn from the reactor in a gaseous state together with the gaseous ethylene cycle. A portion of the linear alpha olefin products remains in the liquid phase of the oligomerization reactor and has to be removed from the reactor via the product outlet line. In a continuous steady state operation, the liquid linear alpha olefins can be removed from the reactor via the product outlet line and the related control valve actuated by the level controller, ensuring a constant liquid level in the reactor. The first portion of the product outlet line can be configured to receive the oligomerization product stream from the oligomerization reactor, and the second portion can be configured to provide the oligomerization product stream to a separation system (18). In some embodiments, the separation system can comprise one or more distillation columns, a thin film vaporizer, a wiped film vaporizer, a falling film vaporizer, or a combination comprising at least one of the foregoing. The first and second portions of the product outlet line can each independently have a predetermined length, $L_1$ and $L_2$, respectively. The lengths $L_1$ and $L_2$ can be minimized lengths. In some embodiments, the second portion of the product outlet line can have a length of 50 to 100 meters.

In some embodiments, the method can further include contacting the discharged oligomerization product stream with a deactivation medium (20). The deactivation medium can be, for example, a catalyst deactivation medium. A catalyst deactivation medium can include, for example, amines, alcohols, or a combination comprising at least one of the foregoing. In some embodiments, the catalyst deactivation medium can include mono alcohols, diols, polyols, or mixtures thereof. In some embodiments, the catalyst deactivation medium is a $C_{2-20}$ mono alcohol. In some embodiments, the catalyst deactivation medium is ethanol, propanol, butanol, a pentanol, a hexanol, a heptanol, an octanol, and nonanol, a decanol, a undecanol, or a combination comprising at least one of the foregoing. In some embodiments, the catalyst deactivation medium is 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, or a combination comprising at least one of the foregoing. Water can also be used as a catalyst deactivation medium.

Contacting of the product stream with the deactivation medium can occur at a predetermined distance from the oligomerization reactor outlet, shown as $L_3$ in FIG. 1. In some embodiments, the distance $L_3$ can be desirably minimized, for example, the distance $L_3$ can be 0.5 to 2 meters. Stated another way, the contacting of the product stream with the deactivation medium can occur at a distance of 0.5 to 2 meters downstream from the oligomerization reactor outlet.

As previously described herein, the method can include heating the oligomerization product stream, heating a wall of the product outlet line, or both, to a temperature greater than the melting temperature of the polymer byproduct.

In some embodiments, the method can include heating a wall of the product outlet line. In some embodiments, at least a portion of the product outlet line (12) can comprise a concentric double pipe having an inner tube and an outer tube surrounding the inner tube. The oligomerization product stream can be present in the inner tube, and the outer tube can include a heating medium. The heating medium can be steam. The presence of the heating medium in the outer tube can be effective to heat a wall of the inner tube comprising the oligomerization product stream. Thus, the oligomerization product stream can be heated to above the melting temperature of a polymer byproduct present in the product stream. In some embodiments, the first portion of the product outlet line, the second portion of the product outlet line, or both the first and the second portions of the product line can comprise the concentric double pipe. In some embodiments, the second portion of product outlet line comprises the concentric double pipe.

In some embodiments, at least a portion of the product outlet line (12) can be heat traced. When present, the heat tracing can be electric heat tracing or steam heat tracing, but is desirably electric heat tracing.

In some embodiments, the oligomerization product stream can be heated in a heat exchanger. When present, the heat exchanger can be positioned at a distance of 1 to 10 meters from the outlet of the oligomerization reactor.

In some embodiments, the oligomerization product stream is formed from oligomerization of an olefin, and the oligomerization product stream comprises solvent, linear alpha olefins, a polymer byproduct, or a combination comprising at least one of the foregoing. The olefin can include any compound having 2 to 30 carbon atoms and at least one olefinic double bond. For example, the olefin can be ethylene, propylene, 1-butene, 2-butene, isobutylene, 1-pentene, 2-pentene, 1-hexene, 2-hexene, 3-hexene, 1-heptene, 2-heptene, 3-heptene, and the like, or a combination comprising at least one of the foregoing. In some embodiments, the olefin used in the oligomerization process is ethylene. The linear alpha olefin products can generally be addition products containing greater than or equal to two ethylene units, but not as many ethylene units as in the relatively high molecular weight addition product referred to as polyethylene. In some embodiments, the oligomerization is a selective oligomerization process, for example a selective ethylene trimerization or tetramerization process. In some embodiments, the oligomerization is a trimerization process. In some embodiments, the linear alpha olefin products comprise $C_{4-12}$ linear alpha olefins. In some embodiments, the linear alpha olefin products comprise $C_{4-8}$ linear alpha olefins. For example, the linear alpha olefins can include at least one of 1-butene, 1-hexene, or 1-octene.

The polymer byproduct can include polyethylene. Polyethylene as used herein refers to relatively high molecular weight polymers of ethylene, and includes copolymers. The term polyethylene can also include linear, branched, and crosslinked polyethylenes. In some embodiments, the polyethylene byproduct can have a weight average molecular weight (Mw) of 50,000 to 10,000,000 Daltons. In some embodiments, the purge stream from the flushing cycle can further comprise heavy fractions (e.g., greater than $C_{12}$ olefins), waxes, and the like, or a combination comprising at least one of the foregoing, in addition to the polyethylene.

The solvent can be any organic solvent capable of dissolving the reaction components. The solvent can be non-reactive with the catalyst composition. Examples of desirable organic solvents can include, but are not limited to, aromatic hydrocarbon solvents which can be unsubstituted or substituted, for example, toluene, benzene, ethyl benzene, xylene, mesitylene, monochlorobenzene, dichlorobenzene, chlorotoluene, isopropyl benzene, aliphatic paraffin hydrocarbons, for example, pentane, hexane, heptane, octane, nonane, decane, alicyclic hydrocarbon compounds, for example, cyclohexane, decahydronaphthalene, and halogenated alkanes, for example, dichloroethane and dichlorobutane, or a combination comprising at least one of the foregoing. In some embodiments, the solvent can be toluene, xylene, mesitylene, benzene, ethylbenzene, isopropyl benzene, or a combination comprising at least one of the foregoing.

In some embodiments, the oligomerization product stream can further comprise residual olefin, a residual catalyst, or a combination comprising at least one of the foregoing. The residual catalyst can be any catalyst system that can oligomerize ethylene.

For example, the catalyst composition can include a chromium source, a heteroatomic multidentate ligand, an activator (also known as a co-catalyst), and optionally, a modifier. A catalyst modifier is not required, but is preferably present.

The chromium compound can be an organic or inorganic salt, coordination complex, or organometallic complex of Cr(II) or Cr(III). In some embodiments the chromium compound is $CrCl_3(tetrahydrofuran)_3$, Cr(III)acetylacetonate, Cr(III)octanoate, chromium hexacarbonyl, Cr(III)-2-ethylhexanoate, benzene(tricarbonyl)-chromium, or Cr(III)chloride. A combination of different chromium compounds can be used.

The heteroatomic multidentate ligand includes two or more heteroatoms (P, N, O, S, As, Sb, Bi, O, S, or Se) that can be the same or different, wherein the two or more heteroatoms are linked via a linking group. The linking group is a $C_{1-6}$ hydrocarbylene group or one of the foregoing heteroatoms. Any of the heteroatoms in the ligand can be substituted to satisfy the valence thereof, with a hydrogen, halogen, $C_{1-18}$ hydrocarbyl group, $C_{1-10}$ hydrocarbylene group linked to the same or different heteroatoms to form a heterocyclic structure, amino group of the formula $NR^aR^b$ wherein each of $R^a$ and $R^b$ is independently hydrogen or a $C_{1-18}$ hydrocarbyl group, a silyl group of the formula $SiR^aR^bR^c$ wherein each of $R^a$, $R^b$, and $R^c$ is independently hydrogen or a $C_{1-18}$ hydrocarbyl group, or a combination comprising at least one of the foregoing substituents. The heteroatoms of the multidentate ligand are preferably a combination comprising phosphorus with nitrogen and sulfur or a combination comprising phosphorous and nitrogen, linked by at least one additional phosphorus or nitrogen heteroatom. In certain embodiments, the ligand can have the backbone PNP, PNPN, NPN, NPNP, NPNPN, PNNP, or cyclic derivatives containing these backbones wherein one or more of the heteroatoms is linked by a $C_{1-10}$ hydrocarbylene to provide a heterocyclic group. A combination of different ligands can be used.

In some embodiments, the ligand has the backbone PNPNH, which as used herein has the general structure $R^1R^2P-N(R^3)-P(R^4)-N(R^5)-H$ wherein each of $R^1$, $R^2$, $R^3$, $R^4$, and $R^5$ is independently a hydrogen, halogen, $C_{1-18}$ hydrocarbyl group, amino group of the formula $NR^aR^b$ wherein each of $R^a$ and $R^b$ is independently hydrogen or a $C_{1-18}$ hydrocarbyl group, a silyl group of the formula $SiR^a R^bR^c$ wherein each of $R^a$, $R^b$, and $R^c$ is independently hydrogen or a $C_{1-18}$ hydrocarbyl group, or two of $R^1$, $R^2$, $R^3$, $R^4$, $R^5$, $R^a$, or $R^b$ taken together are a substituted or unsubstituted $C_{1-10}$ hydrocarbylene group linked to the same or different heteroatoms to form a heterocyclic structure. Exemplary ligands having a heterocyclic structure include the following

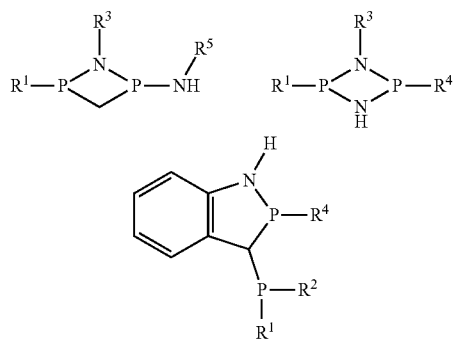

wherein $R^1$, $R^2$, $R^3$, $R^4$, $R^5$ are as described above. In a specific embodiment, each $R^1$, $R^2$, $R^3$, $R^4$, $R^5$ are independently hydrogen, substituted or unsubstituted $C_1-C_8$ alkyl, substituted or unsubstituted $C_6-C_{20}$ aryl, more preferably unsubstituted $C_1-C_6$ alkyl or unsubstituted $C_6-C_{10}$ aryl. A specific example of the ligand is $(phenyl)_2PN(iso-propyl)P$ (phenyl)N(iso-propyl)H, commonly abbreviated $Ph_2PN(i-Pr)P(Ph)NH(i-Pr)$.

Activators can include aluminum compounds, for example a tri($C_1-C_6$alkyl) aluminum such as triethyl aluminum, ($C_1-C_6$ alkyl) aluminum sesquichloride, di($C_1-C_6$alkyl) aluminum chloride, or ($C_1-C_6$-alkyl) aluminum dichloride, or an aluminoxane such as methylaluminoxane (MAO). Each alkyl group can be the same or different, and in some embodiments is methyl, ethyl, isopropyl, or isobutyl. A combination of different activators can be used.

As is known in the art, the modifier can modify the activator, and serve as a chlorine source. Modifiers can include an ammonium or phosphonium salt of the type $(H_4E)X$, $(H_3ER)X$, $(H_2ER_2)X$, $(HER_3)X$, or $(ER_4)X$ wherein E is N or P, X is Cl, Br, or I, and each R is independently a $C_1-C_{22}$ hydrocarbyl, preferably a substituted or unsubstituted $C_1-C_{16}$-alkyl, $C_2-C_{16}$-acyl, or substituted or unsubstituted $C_6-C_{20}$-aryl. In some embodiments the modifier is dodecyltrimethylammonium chloride or tetraphenylphosphonium chloride.

The catalyst composition is often pre-formed (i.e., formed prior to contacting other reaction components in the oligomerization reactor), for example by combining the components in a solvent before contacting with ethylene in an oligomerization process. Examples of solvents that can be used include toluene, benzene, ethylbenzene, cumenene, xylenes, mesitylene, $C_4-C_{15}$ paraffins, cyclohexane, $C_4-C_{12}$ olefins such as butene, hexene, heptene, octene, or ethers or multiethers such as diethylether, tetrahydrofuran, dioxane, di($C_1-C_8$ alkyl)ethers. In some embodiments the solvent is an aromatic solvent such as toluene.

The type of each component selected for use in the catalyst composition and relative amount of each component depend on the desired product and desired selectivity. In some embodiments, the concentration of the chromium compound is 0.01 to 100 millimole per liter (mmol/l), or 0.01 to 10 mmol/l, or 0.01 to 1 mmol/l, or 0.1 to 1.0 mmol/l; and the mole ratio of multidentate ligand:Cr compound:activator is 0.1:1:1 to 10:1:1,000, or 0.5:1:50 to 2:1:500, or 1:1:100 to 5:1:300. Suitable catalyst systems are described, for example, in EP2489431 B1; EP2106854 B1; and WO2004/056479.

In some embodiments, the residual catalyst can include a zirconium-containing catalyst and an organoaluminum co-catalyst. The zirconium-containing catalyst can be a zirconium carboxylate having the formula $Zr(OOCR)_m X_{4-m}$, where R is alkyl, alkenyl, aryl, aralkyl or cycloalkyl, X is halide, for example X is chlorine or bromine, and m is 0 to 4. For example, R can be an alkyl group having 1 to 20 carbon atoms, for example, 1 to 5 carbon atoms. For example, the catalyst can be zirconium tetraisobutyrate. The organoaluminum compound can be, for example, an alkyl aluminum halide. The organoaluminum compound can be of the formula $R'_n\text{—}AlX_{3-n}$, wherein R' is a $C_{1-20}$ alkyl and X is a halide, preferably chlorine or bromine, and n is 1 or 2. In some embodiments, the co-catalyst can comprise ethylaluminum sesquichloride (EASC), diethyl aluminum chloride (DEAC), or a combination comprising at least one of the foregoing.

In a particular embodiment, the method for processing the oligomerization product stream comprises discharging the oligomerization product stream from an oligomerization reactor through a product outlet line having a first portion and a second portion, wherein the first and the second portions each independently have a predetermined length. The first portion is configured to receive the oligomerization product stream from the oligomerization reactor, and the second portion is configured to provide the oligomerization product stream to a separation system, the second portion desirably having a length of 50 to 100 meters. The first and second portions are connected by a control valve. The oligomerization product stream comprises solvent, linear alpha olefins, residual olefin, residual catalyst, a polymer byproduct, or a combination comprising at least one of the foregoing. The method further comprises contacting the oligomerization product stream with a deactivation medium, wherein the contacting occurs at a minimum distance from the oligomerization reactor outlet, desirably at a distance of 0.5 to 2.0 meters downstream from the oligomerization reactor. The oligomerization product stream is heated in a heat exchanger, by heating a wall of the product outlet line, or both, to a temperature of 130 to 200° C., or 150 to 200° C. The method further comprises separating the linear alpha olefins from the oligomerization product stream in the separation system.

The method for processing an oligomerization product stream can advantageously be used in conjunction with any known oligomerization process. Accordingly, another embodiment is a process for the oligomerization of an olefin. The process can include feeding an olefin, solvent, and a catalyst composition into a reactor and oligomerizing the olefin in the reactor to form an oligomerization product stream comprising linear alpha olefins, solvent, a polymer byproduct, or a combination comprising at least one of the foregoing.

The olefin, solvent, and catalyst composition can be as described above. For example, the olefin can be ethylene, and the solvent can be toluene, xylene, mesitylene, benzene, ethylbenzene, isopropyl benzene, or a combination comprising at least one of the foregoing. The catalyst composition can include a chromium source, a heteroatomic multidentate ligand, an activator, and optionally, a modifier. In some embodiments, the catalyst composition can include a zirconium-containing catalyst and an organoaluminum co-catalyst.

The reactor can be any oligomerization reactor. For example, the reactor can be a loop reactor, a plug flow reactor, a bubble column reactor, or a tubular reactor.

The oligomerization process includes oligomerizing the olefin in the reactor to form an oligomerization product stream. The linear alpha olefins can be as described above and can include, for example, $C_{4-12}$ linear alpha olefins. In some embodiments, the process can be adapted to be a selective oligomerization process, for example a selective ethylene trimerization or tetramerization process.

Oligomerization can occur at temperatures of 10 to 200° C., for example, 20 to 100° C., for example, 50 to 90° C., for example, 55 to 80° C., for example, 60 to 70° C. Operating pressures can be 1 to 5 MegaPascals (MPa), for example, 2 to 4 MPa. The process can be continuous and mean residence times can be 10 minutes to 20 hours, for example 30 minutes to 4 hours, for example, 1 to 2 hours. Residence times can be chosen so as to achieve the desired conversion at high selectivity.

Subsequent to oligomerizing the olefin, the oligomerization product stream can be discharged from the oligomerization reactor. The discharged oligomerization product stream can be processed according to the methods described above to reduce or prevent fouling or plugging of the reactor piping with polymer byproduct present in the oligomerization product stream. Desirably, the oligomerization product stream is heated, for example in a heat exchanger or the wall of the outlet piping is heated to a temperature greater than the melting point of the polymer byproduct, for example, to a temperature of greater than or equal to 130° C., but desirably not exceeding 200° C.

The present disclosure provides an improved method for processing an oligomerization product stream. The use of the method described herein can advantageously reduce or eliminate fouling or plugging of high molecular weight polymer byproducts on the wall of the reactor piping by heating to a temperature above the melting point of the polymer byproducts. Thus, the on-stream time of an oligomerization reactor can be increased, therefore minimizing production loss due to reactor downtime. Additionally, effort and cost for additional reactor cleaning are reduced due to longer operation time between reactor shutdown for cleaning. Therefore, a substantial improvement in the processing of an oligomerization product stream is provided.

The methods described herein include at least the following embodiments, which are non-limiting.

Embodiment 1: A method for processing an oligomerization product stream, the method comprising: discharging the oligomerization product stream from an oligomerization reactor through a product outlet line, wherein the oligomerization product stream comprises solvent, linear alpha olefins, a polymer byproduct, or a combination comprising at least one of the foregoing; and heating the oligomerization product stream, heating a wall of the product outlet line, or both, to a temperature greater than the melting temperature of the polymer byproduct.

Embodiment 2: The method of embodiment 1, wherein the product outlet line has a first portion and a second portion, wherein the first portion is configured to receive the oligomerization product stream from the oligomerization reactor, the second portion is configured to provide the oligomerization product stream to a separation system, the first and the second portions each independently have a predetermined length, and the first and second portions are connected by a control valve.

Embodiment 3: The method of embodiment 1 or 2, further comprising contacting the oligomerization product stream with a deactivation medium, wherein the contacting occurs at a minimum distance from the oligomerization reactor outlet, preferably at a distance of 0.5 to 2.0 meters downstream from the oligomerization reactor.

Embodiment 4: The method of embodiment 2 or embodiment 3, wherein the second portion of the product outlet line has a minimum length, preferably a length of 50 to 100 meters.

Embodiment 5: The method of any of embodiments 1 to 4, wherein the heating comprises heating a wall of the product outlet line.

Embodiment 6: The method of any of embodiments 1 to 5, wherein at least a portion of the product outlet line comprises a concentric double pipe having an inner tube and an outer tube surrounding the inner tube, wherein the oligomerization product stream is present in the inner tube, and the outer tube comprises a heating medium, preferably steam, to heat a wall of the inner tube comprising the oligomerization product stream.

Embodiment 7: The method of embodiment 6, wherein the first portion of the product outlet line, the second portion of the product outlet line, or both comprise the concentric double pipe.

Embodiment 8: The method of any of embodiments 1 to 7, wherein at least a portion of the product outlet line is heat traced.

Embodiment 9: The method of any of embodiments 1 to 8, wherein the heating comprises heating the oligomerization product stream in a heat exchanger, wherein the heat exchanger is positioned 1 to 10 meters from the oligomerization reactor.

Embodiment 10: The method of any of embodiments 1 to 9, comprising heating the oligomerization product stream, heating the tube wall of the product outlet line, or both, to a temperature of 130 to 200° C., or 150 to 200° C.

Embodiment 11: The method of any of embodiments 1 to 10, wherein the control valve is a rotary plug valve.

Embodiment 12: The method of any of embodiments 1 to 11, wherein the oligomerization product stream further comprises a residual olefin, residual catalyst, or a combination comprising at least one of the foregoing.

Embodiment 13: The method of embodiment 12, wherein the residual olefin comprises ethylene.

Embodiment 14: The method of any of embodiments 1 to 13, wherein the linear alpha olefins comprise $C_{4-18}$ linear alpha olefins.

Embodiment 15: The method of any of embodiments 1 to 14, wherein the oligomerization product stream is formed from oligomerization of an olefin, preferably wherein the oligomerization is a selective trimerization or tetramerization, preferably a selective trimerization.

Embodiment 16: The method of any of embodiments 1 to 15, wherein the solvent is an aromatic solvent, preferably toluene, xylene, mesitylene, benzene, ethylbenzene, isopropyl benzene or a combination comprising at least one of the foregoing.

Embodiment 17: The method of any of embodiments 12 to 16, wherein the residual catalyst comprises a chromium source, a heteroatomic multidentate ligand, an activator and, optionally, a modifier, preferably wherein the chromium source is at least one of $CrCl_3(tetrahydrofuran)_3$, Cr(III) acetylacetonate, Cr(III)octanoate, chromium hexacarbonyl, Cr(III)-2-ethylhexanoate, benzene(tricarbonyl)-chromium, or Cr(III)chloride; the heteroatomic multidentate ligand is $(phenyl)_2PN(iso-propyl)P(phenyl)N(iso-propyl)H$; the activator is a tri($C_{1-6}$ alkyl) aluminum; and the modifier comprises tetraphenylphosphonium chloride, tetraethylammonium chloride-monohydrate, tetraethylammonium chloride, dodecyltrimethylammonium chloride, isopropylamine hydrochloride, triethylamine hydrochloride, tetrapropylammonium chloride, tetra-n-butylammonium chloride, tetraethylammonium bromide, p-toluidine hydrochloride, dimethyldistearylammonium chloride, (tri-n-butyl)-n-tetradecylphosphonium chloride, benzoyl chloride and acetyl chloride, or a combination comprising at least one of the foregoing.

Embodiment 18: The method of any of embodiments 12 to 16, wherein the residual catalyst comprises a zirconium-containing catalyst and an organoaluminum co-catalyst.

Embodiment 19: The method of any of embodiments 1 to 18, wherein the polymer byproduct comprises polyethylene.

Embodiment 20: A method for processing an oligomerization product stream, the method comprising: discharging the oligomerization product stream from an oligomerization reactor through a product outlet line having a first portion and a second portion, wherein the first and the second portions each independently have a predetermined length; wherein the first portion is configured to receive the oligomerization product stream from the oligomerization reactor; the second portion is configured to provide the oligomerization product stream to a separation system, the second portion preferably having a length of 50 to 100 meters; the first and second portions are connected by a control valve; and the oligomerization product stream comprises solvent, linear alpha olefins, residual olefin, residual catalyst, a polymer byproduct, or a combination comprising at least one of the foregoing; contacting the oligomerization product stream with a deactivation medium, wherein the contacting occurs at a minimum distance from the oligomerization reactor outlet, preferably at a distance of 0.5 to 2.0 meters downstream from the oligomerization reactor; heating the oligomerization product stream in a heat exchanger, heating a wall of the product outlet line, or both, to a temperature of 130 to 200° C., or 150 to 200° C.; and separating the linear alpha olefins from the oligomerization product stream in the separation system.

The methods can alternatively comprise, consist of, or consist essentially of, any appropriate components or steps herein disclosed. The methods can additionally, or alternatively, be formulated so as to be devoid, or substantially free, of any steps, components, materials, ingredients, adjuvants, or species that are otherwise not necessary to the achievement of the function or objectives of the methods.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments. "Optional" or "optionally" means that the subsequently described event or circumstance can or cannot occur, and that the description includes instances where the event occurs and instances where it does not.

As used herein, the term "hydrocarbyl" includes groups containing carbon, hydrogen, and optionally one or more heteroatoms (e.g., 1, 2, 3, or 4 atoms such as halogen, 0, N, S, P, or Si). "Alkyl" means a branched or straight chain, saturated, monovalent hydrocarbon group, e.g., methyl, ethyl, i-propyl, and n-butyl. "Aryl" means a monovalent, monocyclic, or polycyclic aromatic group (e.g., phenyl or naphthyl). "Substituted" means that the compound or group is substituted with at least one (e.g., 1, 2, 3, or 4) substituents instead of hydrogen, where each substituent is independently nitro (—$NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g., benzyl), $C_{7-12}$ alkylarylene (e.g, toluyl), $C_{4-12}$ heterocycloalkyl, $C_{3-12}$ heteroaryl, $C_{1-6}$ alkyl sulfonyl (—S(=O)$_2$-alkyl), $C_{6-12}$ arylsulfonyl (—S(=O)$_2$-aryl), or tosyl ($CH_3C_6H_4SO_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for processing an oligomerization product stream, the method comprising:
   discharging the oligomerization product stream from an oligomerization reactor through a product outlet line, wherein the oligomerization product stream comprises a polymer byproduct and at least one of a solvent and linear alpha olefins; and
   heating a wall of the product outlet line to a temperature of 150 to 200° C.

2. The method of claim 1, wherein the product outlet line has a first portion and a second portion, wherein the first portion is configured to receive the oligomerization product stream from the oligomerization reactor, the second portion is configured to provide the oligomerization product stream to a separation system, the first and the second portions each independently have a predetermined length, the first and second portions are connected by a control valve, and the predetermined length of the second portion is a minimized length that is configured to reduce fouling.

3. The method of claim 2, wherein the predetermined length of the second portion is 100 meters or less.

4. The method of claim 1, further comprising contacting the oligomerization product stream with a deactivation medium, wherein the contacting occurs at a minimized distance downstream from the oligomerization reactor outlet, the minimized distance configured to reduce fouling.

5. The method of claim 1, wherein at least a portion of the product outlet line is heat traced.

6. The method of claim 1, wherein at least a portion of the product outlet line comprises a concentric double pipe having an inner tube and an outer tube surrounding the inner tube, wherein the oligomerization product stream is present in the inner tube, and the outer tube comprises a heating medium, to heat a wall of the inner tube comprising the oligomerization product stream.

7. The method of claim 6, wherein the first portion of the product outlet line, the second portion of the product outlet line, or both comprise the concentric double pipe.

8. The method of claim 6, wherein the heating medium is steam.

9. The method of claim 1, wherein the control valve is a rotary plug valve.

10. The method of claim 1, wherein the linear alpha olefins comprise $C_{4-18}$ linear alpha olefins.

11. The method of claim 1, wherein the oligomerization product stream is formed from oligomerization of an olefin.

12. The method of claim 1, wherein the oligomerization product stream further comprises a residual olefin, residual catalyst, or a combination comprising at least one of the foregoing.

13. The method of claim 12, wherein the residual olefin comprises ethylene.

14. The method of claim 12, wherein the residual catalyst comprises a chromium source, a heteroatomic multidentate ligand, an activator and, optionally, a modifier.

15. The method of claim 12, wherein the residual catalyst comprises a zirconium-containing catalyst and an organoaluminum co-catalyst.

16. The method of claim 1, wherein the solvent is an aromatic solvent.

17. The method of claim 1, wherein the polymer byproduct comprises polyethylene.

18. A method for processing an oligomerization product stream, the method comprising:
   discharging the oligomerization product stream from an oligomerization reactor through a product outlet line having a first portion and a second portion, wherein the first and the second portions each independently have a predetermined length;
   wherein
      the first portion is configured to receive the oligomerization product stream from the oligomerization reactor;
      the second portion is configured to provide the oligomerization product stream to a separation system, the second portion having a length of 100 meters or less;
      the first and second portions are connected by a control valve; and
      the oligomerization product stream comprises solvent, linear alpha olefins, residual olefin, residual catalyst, and a polymer byproduct;
   contacting the oligomerization product stream with a deactivation medium, wherein the contacting occurs at a distance of 2.0 meters or less downstream from the oligomerization reactor outlet;
   heating the oligomerization product stream, heating a wall of the product outlet line, or both, to a temperature of 150 to 200° C.

19. A method for processing an oligomerization product stream, the method comprising:
- discharging the oligomerization product stream from an oligomerization reactor through a product outlet line, wherein the oligomerization product stream comprises a polymer byproduct and at least one of a solvent and linear alpha olefins; and
- heating the oligomerization product stream and heating a wall of the product outlet line to a temperature of 150 to 200° C.;
- wherein the product outlet line has a first portion and a second portion, wherein the first portion is configured to receive the oligomerization product stream from the oligomerization reactor, the second portion is configured to provide the oligomerization product stream to a separation system, the first and the second portions each independently have a predetermined length, and the first and second portions are connected by a control valve;
- wherein the second portion of the product outlet line has a length of 100 meters or less; and
- wherein at least a portion of the product outlet line comprises a concentric double pipe having an inner tube and an outer tube surrounding the inner tube, wherein the oligomerization product stream is present in the inner tube, and the outer tube comprises a heating medium, to heat a wall of the inner tube.

* * * * *